United States Patent
Maeda

(10) Patent No.: US 12,298,245 B2
(45) Date of Patent: May 13, 2025

(54) DETECTION DEVICE, ASSISTANCE DEVICE AND ASSISTANCE METHOD

(71) Applicant: NEC Corporation, Tokyo (JP)

(72) Inventor: Katsumi Maeda, Tokyo (JP)

(73) Assignee: NEC CORPORATION, Tokyo (JP)

( * ) Notice: Subject to any disclaimer, the term of this patent is extended or adjusted under 35 U.S.C. 154(b) by 512 days.

(21) Appl. No.: 17/859,364

(22) Filed: Jul. 7, 2022

(65) Prior Publication Data

US 2023/0096759 A1    Mar. 30, 2023

(30) Foreign Application Priority Data

Jul. 27, 2021   (JP) .................................. 2021-122182

(51) Int. Cl.
| | |
|---|---|
| G01N 21/64 | (2006.01) |
| G01N 21/77 | (2006.01) |
| G01N 33/00 | (2006.01) |
| G06T 7/70 | (2017.01) |
| G06V 10/22 | (2022.01) |
| G06V 10/25 | (2022.01) |
| G06V 20/10 | (2022.01) |
| G06V 20/60 | (2022.01) |

(52) U.S. Cl.
CPC ..... *G01N 21/6456* (2013.01); *G01N 21/6428* (2013.01); *G01N 33/0098* (2013.01); *G06T 7/70* (2017.01); *G06V 10/22* (2022.01); *G06V 20/188* (2022.01); *G01N 2201/022* (2013.01); *G06T 2207/10064* (2013.01); *G06T 2207/30188* (2013.01)

(58) Field of Classification Search
CPC .......... G01N 21/6456; G01N 21/6428; G01N 33/0098; G01N 2201/022; G01N 2021/7786; G01N 21/77; G06T 7/70; G06T 2207/10064; G06T 2207/30188; G06T 7/0012; G06V 10/22; G06V 20/188; G06V 10/25; G06V 20/60
See application file for complete search history.

(56) References Cited

U.S. PATENT DOCUMENTS

| | | | | |
|---|---|---|---|---|
| 6,711,283 | B1* | 3/2004 | Soenksen | H04N 23/631 |
| | | | | 382/128 |
| 12,094,199 | B2* | 9/2024 | Chowdhary | G06V 10/82 |
| 2009/0286263 | A1* | 11/2009 | Graham | C07K 16/065 |
| | | | | 530/389.8 |
| 2021/0088444 | A1* | 3/2021 | Ozaki | G01N 21/6428 |
| 2023/0096759 | A1* | 3/2023 | Maeda | G06T 7/70 |
| | | | | 382/110 |

(Continued)

FOREIGN PATENT DOCUMENTS

WO    WO-2021111621 A1 *  6/2021

OTHER PUBLICATIONS

Real-time monitoring of plant stresses via chemiresistive profiling of leaf volatiles by a wearable sensor Li, Zheng et al. Matter, vol. 4, Issue 7, 2553-2570 (Year: 2021).*

*Primary Examiner* — Gregory A Morse
*Assistant Examiner* — Ronde Lee Miller
(74) *Attorney, Agent, or Firm* — Sughrue Mion, PLLC

(57) ABSTRACT

A detection device according to an aspect of the present disclosure includes a detection portion that contains a substance that emits fluorescence in a case of being irradiated with light when reacting with a plant hormone.

15 Claims, 9 Drawing Sheets

(56) References Cited

U.S. PATENT DOCUMENTS

| | | | |
|---|---|---|---|
| 2023/0292647 A1* | 9/2023 | Bainbridge | G06V 20/188 |
| | | | 702/2 |
| 2024/0037749 A1* | 2/2024 | Rasoulidanesh | G06V 10/806 |
| 2024/0161928 A1* | 5/2024 | Hoveling | A61B 5/418 |
| 2024/0272416 A1* | 8/2024 | Seymour | G16H 10/40 |

* cited by examiner

DETECTION DEVICE, ASSISTANCE DEVICE AND ASSISTANCE METHOD

This application is based upon and claims the benefit of priority from Japanese Patent Application No. 2021-122182, filed on Jul. 27, 2021, the disclosure of which is incorporated herein in its entirety by reference.

TECHNICAL FIELD

The present disclosure relates to a method for detecting plant diseases.

BACKGROUND ART

International Publication No. WO 2021/111621 discloses an example of a method for detecting plant diseases.

A pathological diagnosis system for plants described in International Publication No. WO 2021/111621 performs pathology determination based on a spot of a crop in an image captured by a camera mounted on a drone.

SUMMARY

An object of the present disclosure is to provide a device or the like enabling recognition of the presence of a plant with an early-stage disease.

A detection device according to an aspect of the present disclosure includes a detection portion that contains a substance that emits fluorescence in a case of being irradiated with light when reacting with a plant hormone.

An assistance device according to an aspect of the present disclosure includes: a generation unit that generates position information of a plant infected with a disease based on a captured image of a detection portion irradiated with light and a position of the detection portion, the detection portion containing a substance that emits fluorescence in a case of being irradiated with the light when reacting with a plant hormone; and an output unit that outputs the generated position information.

A terminal device according to an aspect of the present disclosure includes: a receiving unit that receives position information of a plant infected with a disease, the position information being generated based on a captured image of a detection portion irradiated with light and a position of the detection portion, and the detection portion containing a substance that emits fluorescence in a case of being irradiated with the light when reacting with a plant hormone; and a display unit that displays the received position information.

An assistance method according to an aspect of the present disclosure includes: generating position information of a plant infected with a disease based on a captured image of a detection portion irradiated with light and a position of the detection portion, the detection portion containing a substance that emits fluorescence in a case of being irradiated with the light when reacting with a plant hormone; and outputting the generated position information.

A non-transitory computer-readable storage medium according to an aspect of the present disclosure stores a program for causing a computer to execute: generation processing of generating position information of a plant infected with a disease based on a captured image of a detection portion irradiated with light and a position of the detection portion, the detection portion containing a substance that emits fluorescence in a case of being irradiated with the light when reacting with a plant hormone; and output processing of outputting the generated position information.

BRIEF DESCRIPTION OF THE DRAWINGS

Exemplary features and advantages of the present invention will become apparent from the following detailed description when taken with the accompanying drawings in which.

EXAMPLE EMBODIMENT

Hereinafter, example embodiments of the present disclosure will be described in detail with reference to the drawings.

First Example Embodiment

Figure 1:
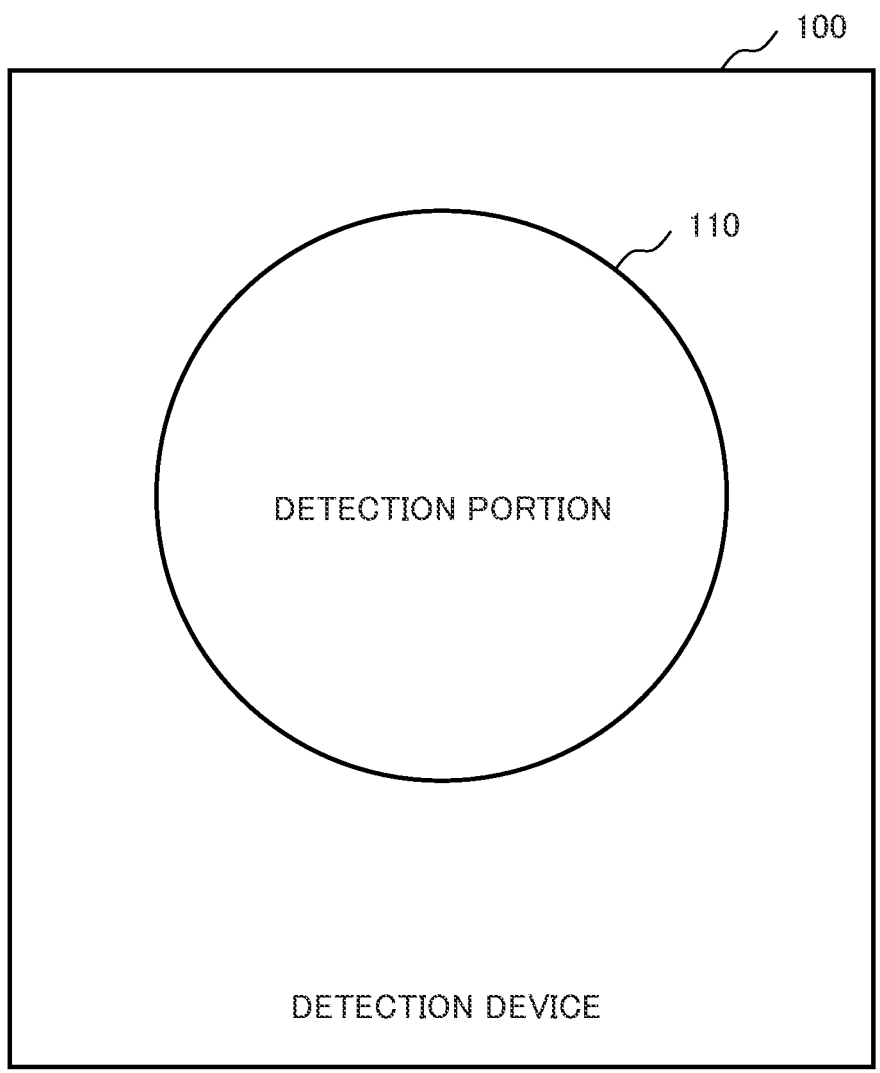
FIG. 1 is a schematic diagram schematically illustrating an example of a configuration of a detection device according to a first example embodiment of the present disclosure.

FIG. 1 is a schematic diagram schematically illustrating an example of a configuration of a detection device according to a first example embodiment of the present disclosure. In the example illustrated in FIG. 1, the detection device 100 includes a detection portion 110.

The detection portion 110 shows a reaction that is in proportion to the amount of infection signal substance of a disease of a plant. Specifically, when the detection portion 110 is irradiated with light, the detection portion 110 irradiated with light emits fluorescence with an intensity that is in proportion to the amount of the infection signal substance that has reacted with the detection portion 110. In the description of the present disclosure, the infection signal substance is also referred to as a plant hormone. The detection portion 110 contains, for example, a substance whose property is changed due to the infection signal substance of a disease of a plant. The infection signal substance is, for example, a substance released from a plant infected with a disease, such as methyl salicylate or methyl jasmonate. The plant disease of the present disclosure is a disease that causes an infected plant to release the infection signal substance. In a case where a plant is infected with a disease (specifically, in a case where a plant is infected with pathogenic bacteria or the like), the plant begins to release the infection signal substance before a visible symptom (for example, a spot caused by a disease of a leaf of the plant, and the like) appears in the plant. In other words, the plant infected with the disease releases the infection signal substance without having the symptom, and then, the symptom appears in the plant (that is, a symptomatic state). Therefore, the present example embodiment has an effect that a plant infected with a disease can be detected before a visible symptom appears in the plant due to the disease.

The substance contained in the detection portion 110 (that is, a substance that emits fluorescence with an intensity that is in proportion to the amount of the reacted infection signal substance such as methyl salicylate or methyl jasmonate) is, for example, at least one of the following substances. Among these substances, a rare earth and a zinc compound emit fluorescence in a case of being irradiated with ultraviolet light having a wavelength of 200 to 400 nanometers (nm). A hydrazine derivative emits fluorescence in a case of being irradiated with ultraviolet light or visible light having a wavelength of 250 to 500 nm. In other words, in a case where, among the substances exemplified below, the rare earth and the zinc compound are used in the detection portion 110, the light with which the detection portion 110 is irradiated is light including ultraviolet light having a wavelength of 200 to 400 nm. In a case where, among the substances exemplified below, the hydrazine derivative is used in the detection portion 110, the light with which the detection portion 110 is irradiated is light including at least one of ultraviolet light or visible light having a wavelength of 250 to 500 nm.

First Substance

A first substance is a boron-oxygen compound having a structure represented by the following General Formula (1) as a receptor that selectively recognizes methyl salicylate.

[Chemical Formula 1]

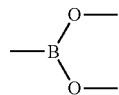

(1)

The boron-oxygen compound may be a diboronic acid derivative represented by the following General Formula (2). (In the following formula, R represents a methyl group, an ethyl group, a propyl group, a butyl group, or a phenyl group, and each R may be the same or different.)

[Chemical Formula 2]

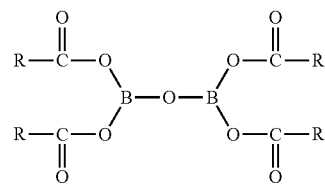

(2)

The boron-oxygen compound may be a phenylboronic acid derivative represented by the following General Formula (3). (In the following formula, X represents a hydrogen molecule, an alkyl group having 1 to 4 carbon atoms, an alkoxy group, a mercapto group, a mercapto-substituted alkyl group, or a mercapto-substituted alkoxy group, n represents an integer of 1 to 5, and when n is equal to or more than 2, each X may be the same or different.)

[Chemical Formula 3]

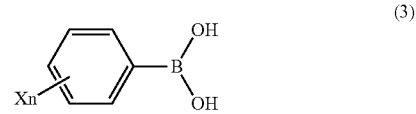

(3)

The boron-oxygen compound may be a boroxine derivative represented by the following General Formula (4). (In the following formula, Z represents an alkyl group having 1 to 4 carbon atoms or a substituted or unsubstituted phenyl group, and each Z may be the same or different.)

[Chemical Formula 4]

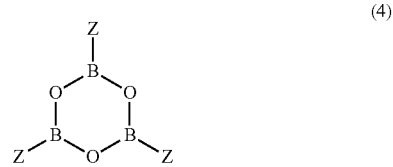

(4)

The first substance emits fluorescence as methyl salicylate reacts with the boron-oxygen compound to form a boron complex.

Second Substance

A second substance is a substance in which the receptor that selectively recognizes methyl salicylate is a rare earth compound.

The above-described rare earth compound may be a compound of any of an acetate, a chloride, an oxalate, a nitrate, a propionate, an isobutyrate, and a pivalate of scandium (Sc), yttrium (Y), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu).

The above-described rare earth compound may be a compound of any of an acetate, a chloride, an oxalate, a nitrate, a propionate, an isobutyrate, or a pivalate of samarium (Sm), europium (Eu), gadolinium (Gd), terbium (Tb), or dysprosium (Dy).

The above-described rare earth compound may be a compound in which a salt of a rare earth element forms a complex with a phosphine oxide derivative.

The above-described rare earth compound emits fluorescence as methyl salicylate reacts with the rare earth compound to form a complex of rare earth.

Third Substance

A third substance is a substance in which the receptor that selectively recognizes methyl salicylate is a zinc compound.

The above-described zinc compound is a compound of any of zinc(II) acetate, zinc(II) formate dihydrate, zinc(II) butyrate, zinc oxalate dihydrate, zinc(II) hexanoate, zinc(II) propionate, zinc(II) tartrate dihydrate, zinc(II) benzoate, zinc(II) octanoate, zinc(II) oleate, zinc(II) nitrate, and zinc (II) chloride.

The above-described zinc compound emits fluorescence as methyl salicylate reacts with the zinc compound to form a complex.

Fourth Substance

A fourth substance is a substance in which the receptor that selectively recognizes methyl jasmonate is a hydrazine derivative.

The above-described hydrazine derivative is a compound of any of 4-hydrazino-7-nitro-2,1,3-benzoxadiazole hydrazine, 5-dimethylaminonaphthalene-1-sulfonyl hydrazine, and 4-(N,N-dimethylaminosulfonyl)-7-hydrazino-2,1,3-benzoxadiazole.

The above-described hydrazine derivative emits fluorescence as methyl jasmonate reacts with the hydrazine derivative to form a hydrazone derivative.

These substances emit fluorescence with an intensity that is in proportion to the amount of methyl salicylate that has reacted with these substances per unit weight in a case of being irradiated with light. The detection portion 110 contains at least one of these substances.

Effects

The present example embodiment has an effect of enabling recognition of the presence of a plant with an early-stage disease. This is because, in a case of being irradiated with light, the detection portion 110 emits fluorescence with an intensity based on the amount of the infection signal substance of a disease of a plant that has reacted with the detection portion 110 per unit area.

Specific Example of First Example Embodiment

The detection device 100 can be implemented by, for example, a base such as a plate to which the detection portion 110 such as a filter paper impregnated with the substance is attached. The material of the base may be a combination of one or more of wood, metal, resin, mineral, and the like. The material of the base is not particularly limited. The shape of the base is not particularly limited. The base may be formed as, for example, a plate, a column, a thread, a string, a cable, a tape, a sheet, or the like. The detection portion 110 may be, for example, an object impregnated with the substance. In this case, the detection portion 110 may be, for example, a filter paper, a cloth, a resin sheet that can be impregnated with the substance, or the like. The detection portion 110 may be the substance applied onto the base or a mixture of the substance and another substance applied onto the base. The shape of the detection portion 110 is not particularly limited. The shape of the detection portion 110 may be a predetermined figure such as a rectangle, a polygon, or a circle. The shape of the detection portion 110 may be a contour line of a predetermined figure having a finite thickness. The shape of the detection portion 110 may be a mark, a character, a character string, or the like. The shape of the detection portion 110 may be a graphic such as a barcode or a quick response (QR) code (registered trademark).

Hereinafter, a more specific example of the detection device 100 will be described.

The detection device 100 may be a resin substrate, a wood substrate, a metal substrate, or the like to which a sheet such as a filter paper impregnated with the substance is attached. The detection device 100 may be a substrate onto which a substance containing the substance is applied. The detection device 100 may be a part of a structure such as a garden stone or a wall to which a sheet such as a filter paper impregnated with the substance is attached. The detection device 100 may be a part of a structure such as a garden stone or a wall onto which a substance including the substance is applied. The detection device 100 may be a tape onto which the substance is applied. The material of the tape is, for example, paper, resin, a combination of paper and resin, or another material that can form the tape. The detection device 100 may be a tape impregnated with the substance. The detection device 100 may be a thread, a string, a cable, an optical fiber, or the like onto which the substance is applied. The optical fiber is an optical fiber configured in such a way that a part of light passing through the inside leaks from the surface. The detection device 100 may be a thread or a string impregnated with the substance. The detection device 100 may be a cable or an optical fiber coated with a substance impregnated with the substance. In a case where the detection device 100 has a portion impregnated with the substance, the portion impregnated with the substance functions as the detection portion 110. In a case where the detection device 100 has a portion onto which the substance is applied, the portion onto which the substance is applied functions as the detection portion 110.

The outline of the detection portion 110 may be drawn by using a fluorescent substance that emits fluorescence when irradiated with light.

Second Example Embodiment

Figure 2:
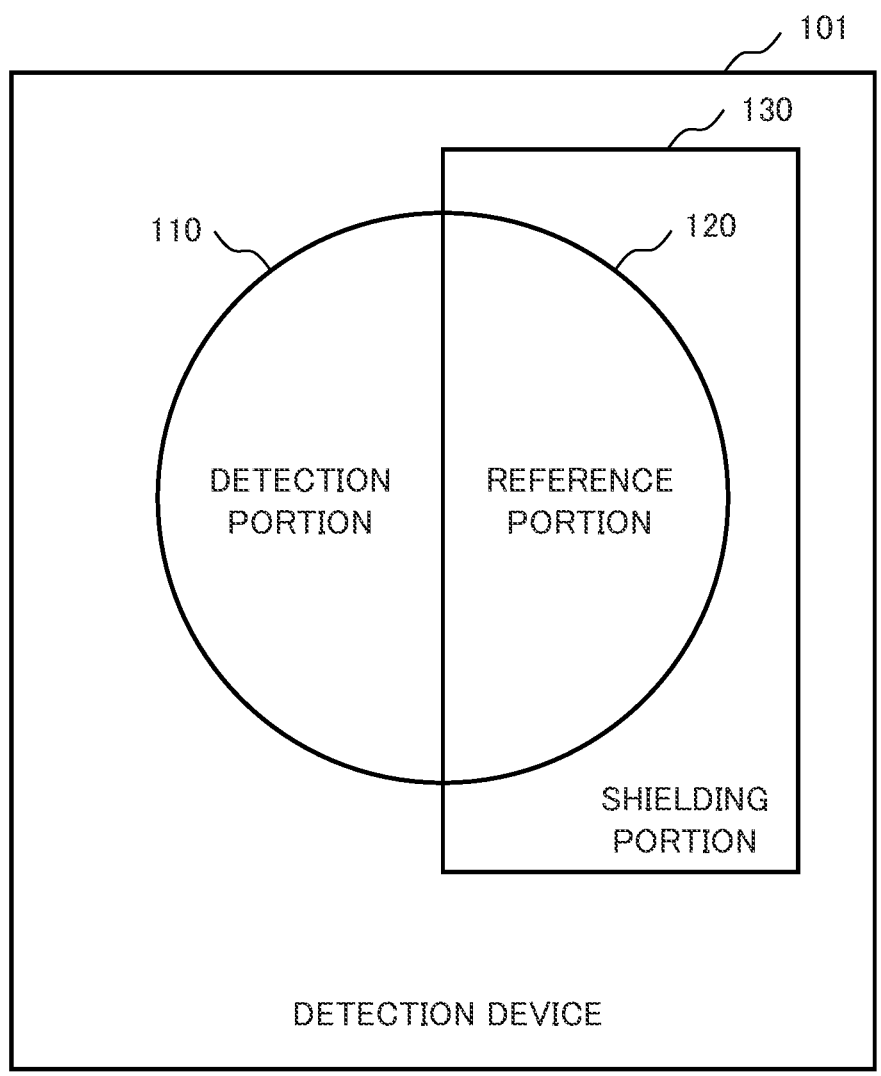
FIG. 2 is a schematic diagram schematically illustrating an example of a configuration of a detection device according to a second example embodiment of the present disclosure.

FIG. 2 is a schematic diagram schematically illustrating an example of a configuration of a detection device according to a second example embodiment of the present disclosure. In the example illustrated in FIG. 2, a detection device 101 includes a detection portion 110, a reference portion 120, and a shielding portion 130. The detection portion 110 and the reference portion 120 of the present example embodiment are the same as the detection portion 110 of the first example embodiment.

The shielding portion 130 is a detachable component that shields the reference portion 120 from the outside air containing the infection signal substance. Specifically, the shielding portion 130 covers the reference portion 120 in such a way that the reference portion 120 is shielded from the outside air except when the shielding portion 130 is removed from the reference portion 120. The shielding portion 130 can suppress a reaction between the substance in the reference portion 120 and the infection signal substance contained in the outside air by covering the reference portion 120. In the description of the present example embodiment, the outside air is air other than air between the shielding portion 130 and the reference portion 120.

Effects

The present example embodiment has the same effects as those of the first example embodiment. The reason is the same as the reason why the effects of the first example embodiment are exhibited.

Specific Example of Second Example Embodiment

The detection device 101 according to the second example embodiment of the present disclosure has a configuration similar to that of the detection device 100 according to the first example embodiment. However, in the portion impregnated with the substance, a portion that is not shielded by the shielding portion 130 may function as the detection portion 110, and a portion that is shielded by the shielding portion 130 may function as the reference portion 120. In the portion onto which the substance is applied, a portion that is not shielded by the shielding portion 130 may function as the detection portion 110, and a portion that is shielded by the shielding portion 130 may function as the reference portion 120. The detection portion 110 and the reference portion 120 may be formed to be separated from each other. The detection portion 110 and the reference portion 120 may be integrally formed.

As described above, the shielding portion 130 is a component that covers the reference portion 120 in such a way that the reference portion 120 is shielded from the outside air, and is detachable from the reference portion 120. The material and shape of the shielding portion 130 are not particularly limited.

The outline of the detection portion 110 may be drawn by using a fluorescent substance that emits fluorescence when irradiated with light. The outline of the reference portion 120 may be drawn by using a fluorescent substance that emits fluorescence when irradiated with light.

Third Example Embodiment

Figure 3:
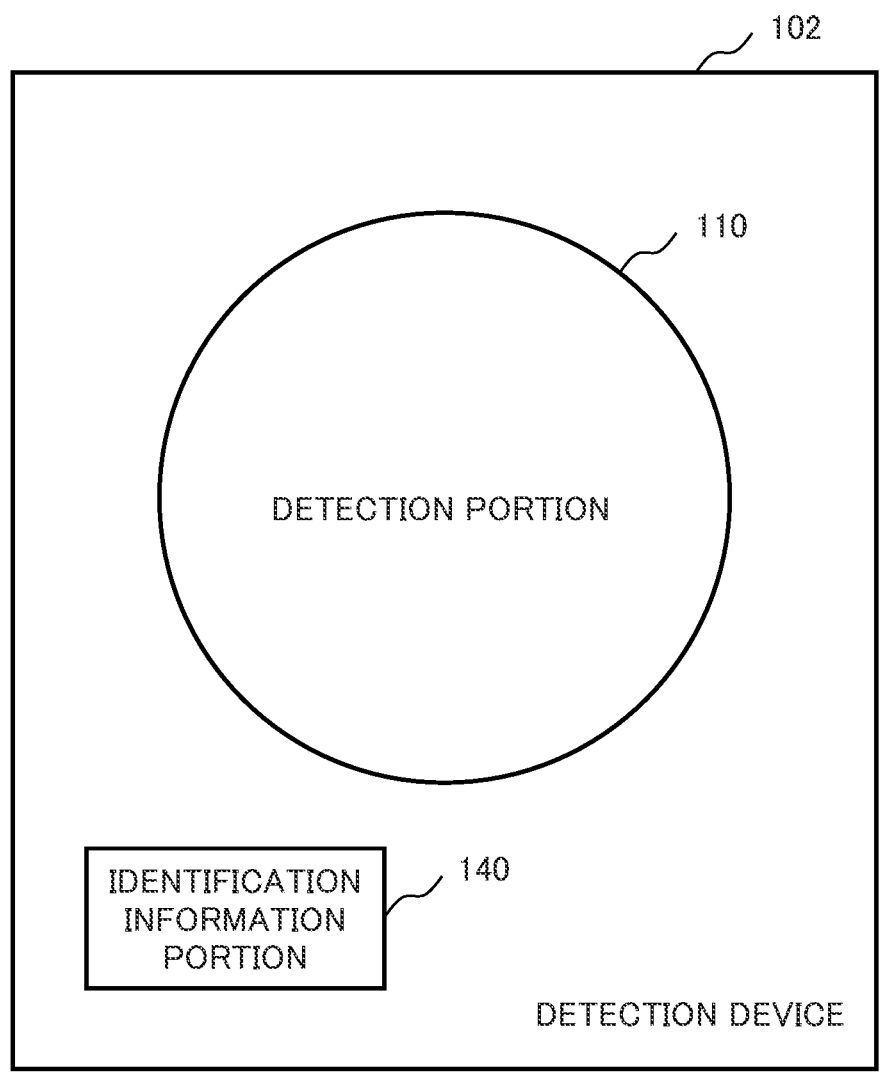
FIG. 3 is a schematic diagram schematically illustrating an example of a configuration of a detection device according to a third example embodiment of the present disclosure.

FIG. 3 is a schematic diagram schematically illustrating an example of a configuration of a detection device 102 according to a third example embodiment of the present disclosure. The detection device 102 includes a detection portion 110 and an identification information portion 140. The detection device 102 may further include a reference portion 120 and a shielding portion 130. The detection portion 110 is the same as the detection portions 110 of the first example embodiment and the second example embodiment. The reference portion 120 and the shielding portion 130 are the same as the reference portion 120 and the shielding portion 130 of the second example embodiment.

The identification information portion 140 holds identification information assigned to the detection device 102 in such a way that the identification information can be read from the outside of the detection device 102. The identification information is information that is assigned to the detection device 102 and can individually specify the detection device 102. The identification information may be, for example, a number such as a serial number. The identification information may be represented by a character string. The identification information may be represented by data. The identification information may be represented by a barcode, a QR code, or the like.

Effects

The present example embodiment has the same effects as those of the first example embodiment. The reason is the same as the reason why the effects of the first example embodiment are exhibited.

Specific Example of Third Example Embodiment

The detection portion 110 of the present example embodiment can be implemented by the specific example of the detection portion 110 described as the specific example of the first example embodiment. The reference portion 120 and the shielding portion 130 of the present example embodiment can be implemented by the reference portion 120 and the shielding portion 130 described as the specific example of the second example embodiment.

The identification information portion 140 may be a portion of the surface of the detection device 102 on which the identification information is drawn. In this case, the identification information is, for example, a number or another character string, a figure, a barcode, a QR code, or the like. In this case, the identification information may be drawn by using a fluorescent substance. The identification information may be drawn by using the substance. In a case where the identification information is drawn by using the substance, the identification information portion 140 may also function as the detection portion 110. The identification information portion 140 may be a radio frequency identifier (RFID) tag holding the identification information.

Fourth Example Embodiment

Hereinafter, a fourth example embodiment of the present disclosure will be described in detail with reference to the drawings.

Configuration

Figure 4:
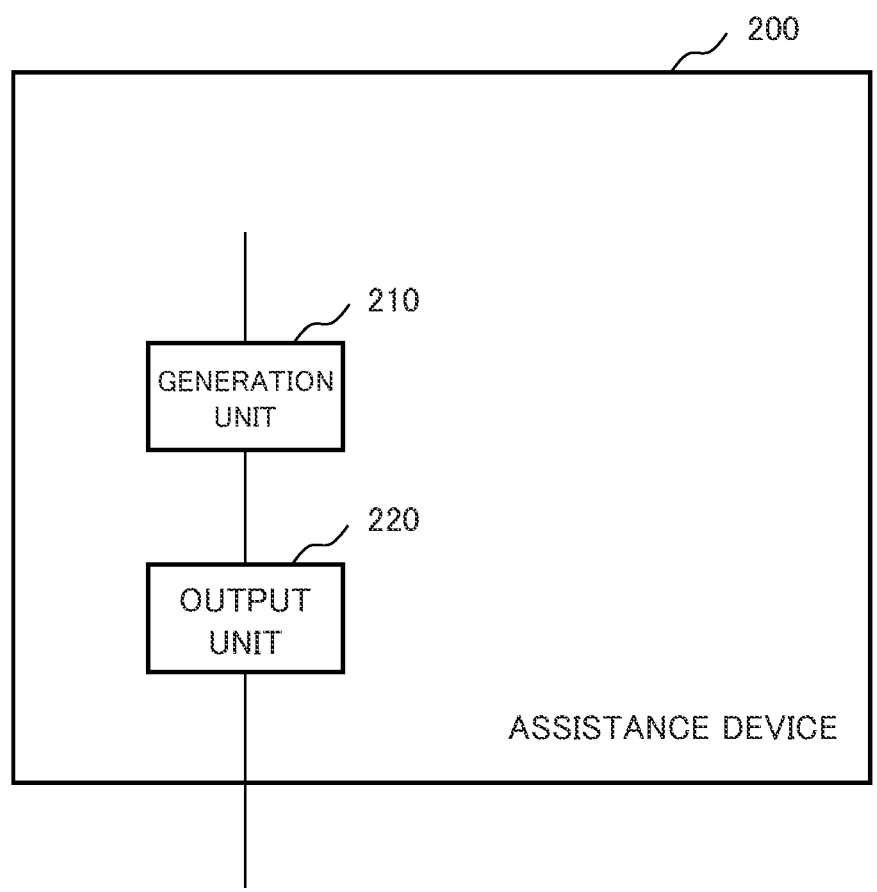
FIG. 4 is a block diagram illustrating an example of a configuration of an assistance device according to a fourth example embodiment of the present disclosure.

FIG. 4 is a block diagram illustrating an example of a configuration of an assistance device 200 according to the fourth example embodiment of the present disclosure. In the example illustrated in FIG. 4, the assistance device 200 includes a generation unit 210 and an output unit 220.

The generation unit 210 generates position information of a plant infected with a disease based on a captured image of the detection portion 110 irradiated with light and a position of the detection portion 110, the detection portion 110 containing a substance that emits fluorescence in a case of being irradiated with the light when reacting with a plant hormone. The detection portion is the detection portion 110 according to any one of the first to third example embodiments described above.

The output unit 220 outputs the generated position information.

For example, the generation unit 210 may estimate information on the amount of the plant hormone at the position of the detection portion 110 from the brightness of the detection portion 110 in the captured image based on a relationship between the brightness of the detection portion 110 irradiated with ultraviolet light and the amount of the plant hormone that has reacted with the detection portion 110. The amount of the plant hormone that has reacted with the detection portion 110 may be, for example, the amount of the plant hormone that has reacted with the detection portion 110 per unit area. For example, the position of the detection device 100 including the detection portion 110 is regarded as the position of the detection portion 110. The amounts of the plant hormone at a plurality of time points are expressed as the trend of the amount of the plant hormone.

In the trend of the amount of the plant hormone that has reacted with the detection portion 110, in a case where a change in amount of the plant hormone exceeds a predetermined value, there is a possibility that a plant infected with a disease exists around the detection portion 110.

For example, the generation unit 210 specifies the detection portion 110 (that is, the detection device 100) around which a plant infected with a disease is likely to exist based on the trend of the amount of the plant hormone that has reacted with the detection portion 110. The generation unit 210 generates the position information of the plant infected with the disease based on the specified position of the detection portion 110.

For example, in a case where the change in amount of the plant hormone exceeds the predetermined value in the trend of the amount of the plant hormone that has reacted with the detection portion 110, the generation unit 210 may specify the detection portion 110 as the detection portion 110 around which a plant infected with a disease is likely to exist. For example, in a case where an increase of the change in amount of the plant hormone exceeds a predetermined value in the trend of the amount of the plant hormone that has reacted with the detection portion 110, the generation unit 210 may specify the detection portion 110 as the detection portion 110 around which a plant infected with a disease is likely to exist. In the following description, the detection portion 110 around which a plant infected with a disease is likely to exist is also referred to as a detection receptor.

The generation unit 210 generates a range based on the position of the detection receptor as information indicating a region where a plant infected with a disease is likely to exist, in other words, the position information of the plant infected with the disease.

The generation unit 210 may generate information indicating the position of the detection receptor (for example, the position of the detection device 100 including the detection receptor) as the position information of the plant infected with the disease. Specifically, the generation unit 210 generates, as the position information of the plant infected with the disease, information of a screen in which a mark (for example, a combination of one or more of a figure, a symbol, a character, a character string, and the like) indicating the position of the detection receptor is superimposed on an image indicating a place in which the plant is cultivated.

For example, the generation unit 210 may specify a region based on a distance from the position of the detection receptor (for example, a place in which the detection device 100 including the detection receptor is installed) as the region where a plant infected with a disease is likely to exist.

In this case, the region based on the distance from the position of the detection receptor may be, for example, a region within a predetermined distance from the position of the detection receptor. The region based on the distance from the position of the detection receptor may be, for example, a region that is at a first predetermined distance or more from the position of the detection receptor and is at a second predetermined distance or less from the position of the detection receptor, the second predetermined distance being larger than the first predetermined distance.

The generation unit 210 may estimate a distance from the detection portion 110 to the plant infected with the disease based on the amount of change in amount of the plant hormone in the trend of the amount of the plant hormone that has reacted with the detection portion 110. In this case, the generation unit 210 holds in advance a relationship between the amount of change in amount of the plant hormone and the distance from the detection portion to the plant infected with the disease, and estimates the distance from the detection portion 110 to the plant infected with the disease based on the relationship.

For example, the generation unit 210 may estimate the distance from the detection portion 110 to the plant infected with the disease based on an increment of the change in amount of the plant hormone in the trend of the amount of the plant hormone that has reacted with the detection portion 110. In this case, the generation unit 210 holds in advance a relationship between the increment of the change in amount of the plant hormone and the distance from the detection portion to the plant infected with the disease, and estimates the distance from the detection portion 110 to the plant infected with the disease based on the relationship.

In this case, the region based on the distance from the position of the detection receptor may be, for example, a region within the estimated distance from the position of the detection receptor. The region based on the distance from the position of the detection receptor may be, for example, a region that is at a third predetermined distance or more from the position of the detection receptor and is at a fourth predetermined distance or less from the position of the detection receptor. However, the third predetermined distance is smaller than the estimated distance, and the fourth predetermined distance is larger than the estimated distance.

For example, the generation unit 210 may specify, among a plurality of divided sections of the place in which the plant is cultivated, a section including a region within a predetermined distance from a place in which the detection device 100 including the detection receptor is installed, as the region where a plant infected with a disease is likely to exist.

In the above case, the generation unit 210 generates, as the position information of the plant infected with the disease, information indicating a region where the plant infected with the disease is likely to exist. Specifically, the generation unit 210 generates information of a screen in which a mark indicating the region where the plant infected with the disease is likely to exist is superimposed on an image indicating the place in which the plant is cultivated. The mark indicating the region where the plant infected with the disease is likely to exist may be a line surrounding the region where the plant infected with the disease is likely to exist. The mark indicating the region where the plant infected with the disease is likely to exist may be a predetermined pattern drawn on the region where the plant infected with the disease is likely to exist. The mark indicating the region where the plant infected with the disease is likely to exist may be changing the color of the region where the plant infected with the disease is likely to exist. The mark indicating the region where the plant infected with the disease is likely to exist is not limited to these examples.

The position information of the infected plant is not limited to the above example as long as it is information indicating a position, a figure, a range, and the like, for example. The position information of the infected plant may be text data or the like.

In the present example embodiment and another example embodiment of the present disclosure, a place (and a region) where a plant is cultivated may be the inside of a greenhouse. The place in which the plant is cultivated may be outdoors.

Operation

Figure 5:
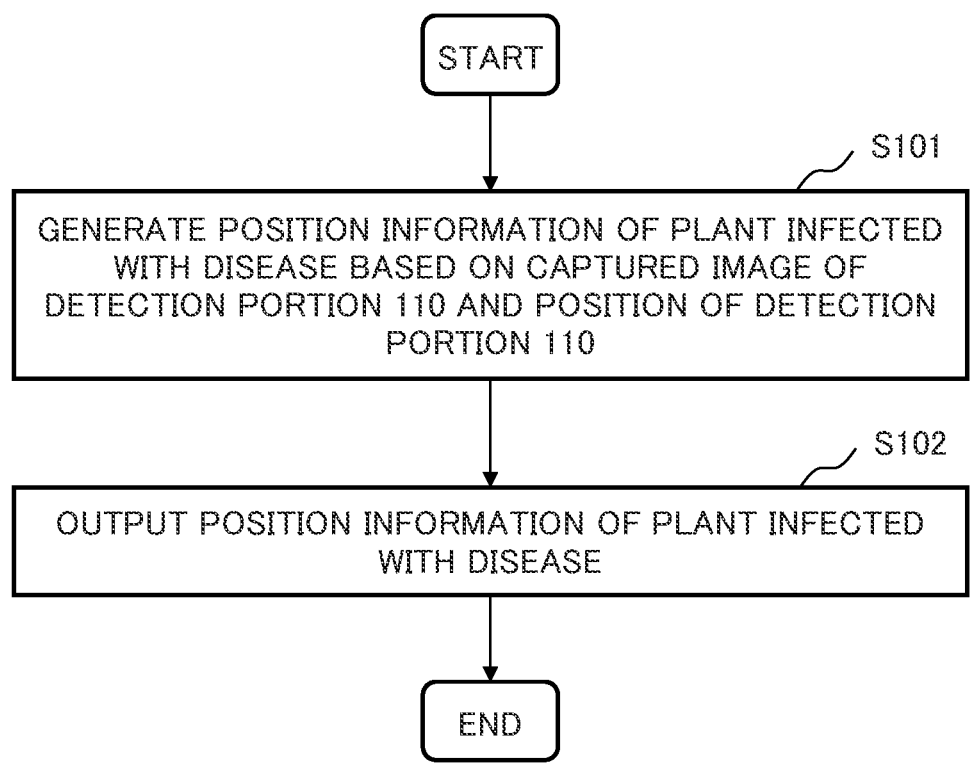
FIG. 5 is a flowchart illustrating an example of an operation of the assistance device according to the fourth example embodiment of the present disclosure.

FIG. 5 is a flowchart illustrating an example of an operation of the assistance device 200 according to the fourth example embodiment of the present disclosure. In the example illustrated in FIG. 5, the generation unit 210 generates the position information of a plant infected with a disease based on a captured image of the detection portion 110 and the position of the detection portion 110 (Step S101). Next, the output unit 220 outputs the position information of the plant infected with the disease (Step S102).

Effects

The present example embodiment has an effect of enabling recognition of the presence of a plant with an early-stage disease. This is because the generation unit 210 generates the position information of the plant infected with the disease based on the captured image of the detection portion 110 and the position of the detection portion 110. In a case of being irradiated with light, the detection portion 110 emits fluorescence with an intensity based on the amount of the infection signal substance of the disease of the plant that has reacted with the detection portion 110 per unit area.

Fifth Example Embodiment

Figure 6:
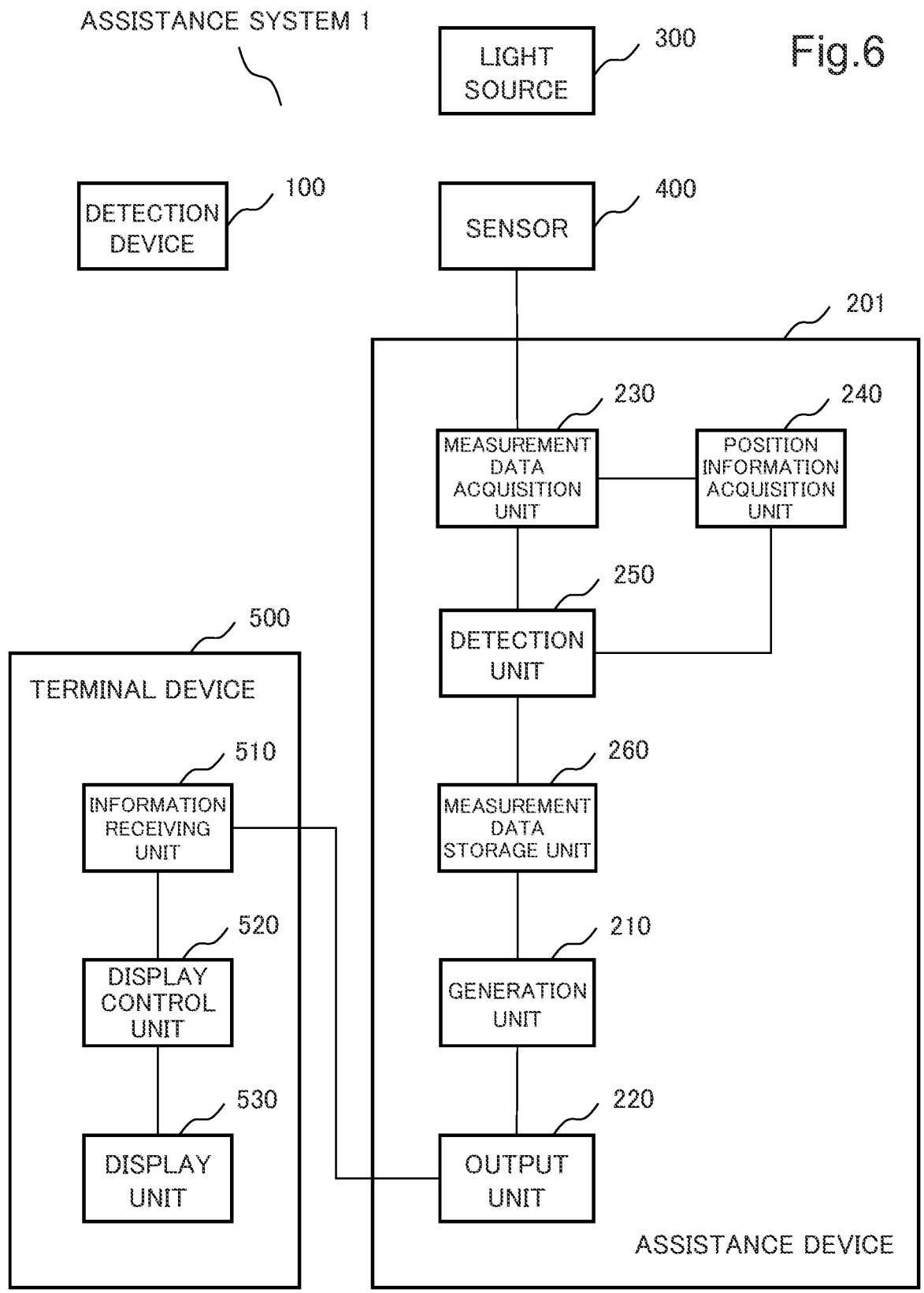
FIG. 6 is a block diagram illustrating an example of a configuration of an assistance system according to a fifth example embodiment of the present disclosure.

FIG. 6 is a block diagram illustrating an example of a configuration of an assistance system according to a fifth example embodiment of the present disclosure. In the example illustrated in FIG. 6, an assistance system 1 includes a plurality of detection devices 100, an assistance device 201, a light source 300, a sensor 400, and a terminal device 500. The assistance device 201 is communicably connected to each of the sensor 400 and the terminal device 500.

The detection device 100 is the detection device 100 according to the first example embodiment.

The light source 300 emits light. The light source 300 is disposed in such a way as to irradiate a detection portion 110 of the detection device 100 with light.

The sensor 400 is, for example, a sensor that measures the brightness of the detection portion 110 of the detection device 100 irradiated with light from the light source 300, obtained by imaging. Specifically, the sensor 400 is, for example, an imaging device that captures an image of the detection device 100 irradiated with light from the light source 300 (specifically, an image of at least a part of the detection portion 110 irradiated with light). The imaging device is, for example, a digital camera, a camera of a smartphone, or the like. The sensor 400 has a function of transmitting a measurement result (for example, an image) to the assistance device 201. The image is a moving image or one or more still images. For example, a worker performs measurement on the detection device 100 by using the sensor 400.

The sensor 400 may be disposed in such a way as to capture an image of the detection device 100 including at least a part of a region of the detection portion 110. The sensor 400 may be disposed in such a way as to capture an image including only the region of the detection portion 110. Note that parameters that affect a relationship between the brightness and color of the detection portion 110 and the brightness and color of the detection portion 110 in the image, such as the aperture, sensitivity, gain, and color temperature of the camera of the sensor 400, are fixed.

<Assistance Device 201>

The assistance device 201 includes a measurement data acquisition unit 230, a position information acquisition unit 240, a detection unit 250, a measurement data storage unit 260, a generation unit 210, and an output unit 220. The generation unit 210 and the output unit 220 of the present example embodiment are the same as the generation unit 210 and the output unit 220 of the fourth example embodiment except for differences described below.

<Measurement Data Acquisition Unit 230>

The measurement data acquisition unit 230 acquires measurement data from the sensor 400. The measurement data is, for example, an image of the detection portion 110 of the detection device 100 obtained by the sensor 400. The measurement data acquisition unit 230 transmits the acquired measurement data (for example, an image) to the detection unit 250.

The measurement data acquisition unit 230 of the present example embodiment may acquire the measurement data of each of the plurality of detection portions 110.

<Position Information Acquisition Unit 240>

The position information acquisition unit 240 acquires the position of the detection portion 110. The position information acquisition unit 240 may acquire the position of the detection device 100 as the position of the detection portion 110. In the present example embodiment, the position information acquisition unit 240 acquires the position information of each of the plurality of detection portions 110.

In the present example embodiment, the position information acquisition unit 240 may acquire, via an input device such as a keyboard or a touch panel, information indicating the position of the detection portion 110, the information being input by an operator of the assistance system 1 using the input device. The information indicating the position of the detection portion 110 may be, for example, a number assigned to the detection portion 110. The information indicating the position of the detection portion 110 may be, for example, a number assigned to the detection device 100 including the detection portion 110. In these cases, a combination of a number that is information indicating a position and position information to which the number is assigned is assigned in advance to the position information acquisition unit 240. Then, the position information acquisition unit 240 specifies, as the position information of the detection portion 110, position information to which a number indicating the acquired position is assigned. The position information may be identification information of a section of a plant cultivation field. The position information may be coordinates in a coordinate system defined in the plant cultivation field. The input information indicating the position of the detection portion 110 may be the position information of the detection portion 110 such as the identification information of the section or the coordinates.

The position information acquisition unit 240 transmits the position information of the detection portion 110 to the detection unit 250. For example, the position information acquisition unit 240 may transmit, as the position information of the detection portion 110, the position information of the detection device 100 to the detection unit 250.

<Detection Unit 250>

The detection unit 250 receives the measurement data (for example, an image) from the measurement data acquisition unit 230. Furthermore, the detection unit 250 receives the position information of the detection portion 110 from the position information acquisition unit 240.

The detection unit 250 detects a region of the detection portion 110 in the received image. In a case where the sensor 400 that is a camera is disposed in such a way as to capture an image including only the region of the detection portion 110, the detection unit 250 detects the entire image as the region of the detection portion 110. Otherwise, for example, the detection unit 250 may calculate the intensity that is in proportion to the intensity of a wavelength (for example, 545 to 546 nm) of fluorescence, from a pixel value of each pixel of the image that is the measurement data. An image in which a pixel shows the intensity of the wavelength of fluorescence is referred to as a fluorescence image. The detection unit 250 extracts the region of the detection portion 110 in the fluorescence image based on the shape of the detection portion 110. In this case, for example, the detection unit 250 may divide the fluorescence image into partial regions having constant brightness, and extract a region having a shape corresponding to a part of the detection portion 110 or the entire detection portion 110 among the partial regions as the region of the detection portion 110.

The detection unit 250 generates the brightness of the region of the detection portion 110. For example, the detection unit 250 specifies, as a value representing the brightness of the region of the detection portion 110, a representative value (an average value, a median value, an intermediate value, a mode value, or the like) of the pixel values of the pixels included in the region of the detection portion 110. Then, the detection unit 250 associates a measurement time and the position information with the value representing the brightness of the region of the detection portion 110, and stores the value representing the brightness of the region of the detection portion 110 and associated with the measurement time and the position information in the measurement data storage unit 260.

In the present example embodiment, the detection unit 250 may individually store, in the measurement data storage unit 260, the value of each of the plurality of detection portions 110, the value representing the brightness of the region of the detection portion 110 and being associated with the measurement time and the position information.

<Measurement Data Storage Unit 260>

The measurement data storage unit 260 stores the trend of the measurement result. The trend of the measurement result is, for example, values representing the brightness of the region of the detection portion 110 and associated with the measurement time and the position information at a plurality of time points. In the present example embodiment, the measurement data storage unit 260 may store the trend of the measurement result of each of the plurality of detection portions 110.

<Generation Unit 210>

The generation unit 210 reads the trend of the measurement result from the measurement data storage unit 260. As described above, the trend of the measurement result is values representing the brightness of the region of the detection portion 110 and associated with the measurement time and the position information at a plurality of time points.

The generation unit 210 estimates the trend of the amount of the plant hormone that has reacted with the detection portion 110 from the trend of the measurement result. The generation unit 210 specifies the detection portion 110 around which a plant infected with a disease is likely to exist, based on the trend of the amount of the plant hormone that has reacted with the detection portion 110. The generation unit 210 generates the position information of the diseased plant based on the position of the detection portion 110 specified as the detection portion 110 around which a plant infected with a disease is likely to exist.

Specifically, for example, the generation unit 210 calculates a change in amount of the plant hormone that has reacted with the detection portion 110 per unit period, from the amount of the plant hormone that has reacted with the detection portion 110 per unit area at least at the latest two time points in the trend of the measurement result. For example, as described above, the generation unit 210 specifies the detection portion 110 around which a plant infected with a disease is likely to exist based on the change in amount of the plant hormone that has reacted with the detection portion 110 per unit period.

In the present example embodiment, the generation unit 210 may specify the detection portion 110 around which a plant infected with a disease is likely to exist among the plurality of detection portions 110. The generation unit 210 may generate the position information of the infected plant as in the example described in the fourth example embodiment for each detection portion 110 specified as the detection portion 110 around which a plant infected with a disease is likely to exist. In the present example embodiment, the generation unit 210 may output information in which a figure that indicates the position information of the infected plant and is generated for the plurality of detection portions 110 is superimposed on an image indicating a region where the plant is cultivated. The mark indicating the position information of the infected plant may be the same as the mark indicating the position information of the infected plant in the fourth example embodiment.

<Output Unit 220>

The output unit 220 outputs the position information of the infected plant to the terminal device 500.

<Terminal Device 500>

The terminal device 500 includes an information receiving unit 510, a display control unit 520, and a display unit 530. The terminal device 500 can be implemented by, for example, a terminal device such as a smartphone, a tablet terminal, or a notebook personal computer.

The information receiving unit 510 receives the position information of the infected plant from the output unit 220 of the assistance device 201. The display control unit 520 controls the display unit 530 to display the received position information of the infected plant. The display unit 530 displays the position information of the infected plant. The display unit 530 is, for example, a display.

Operation

Figure 7:
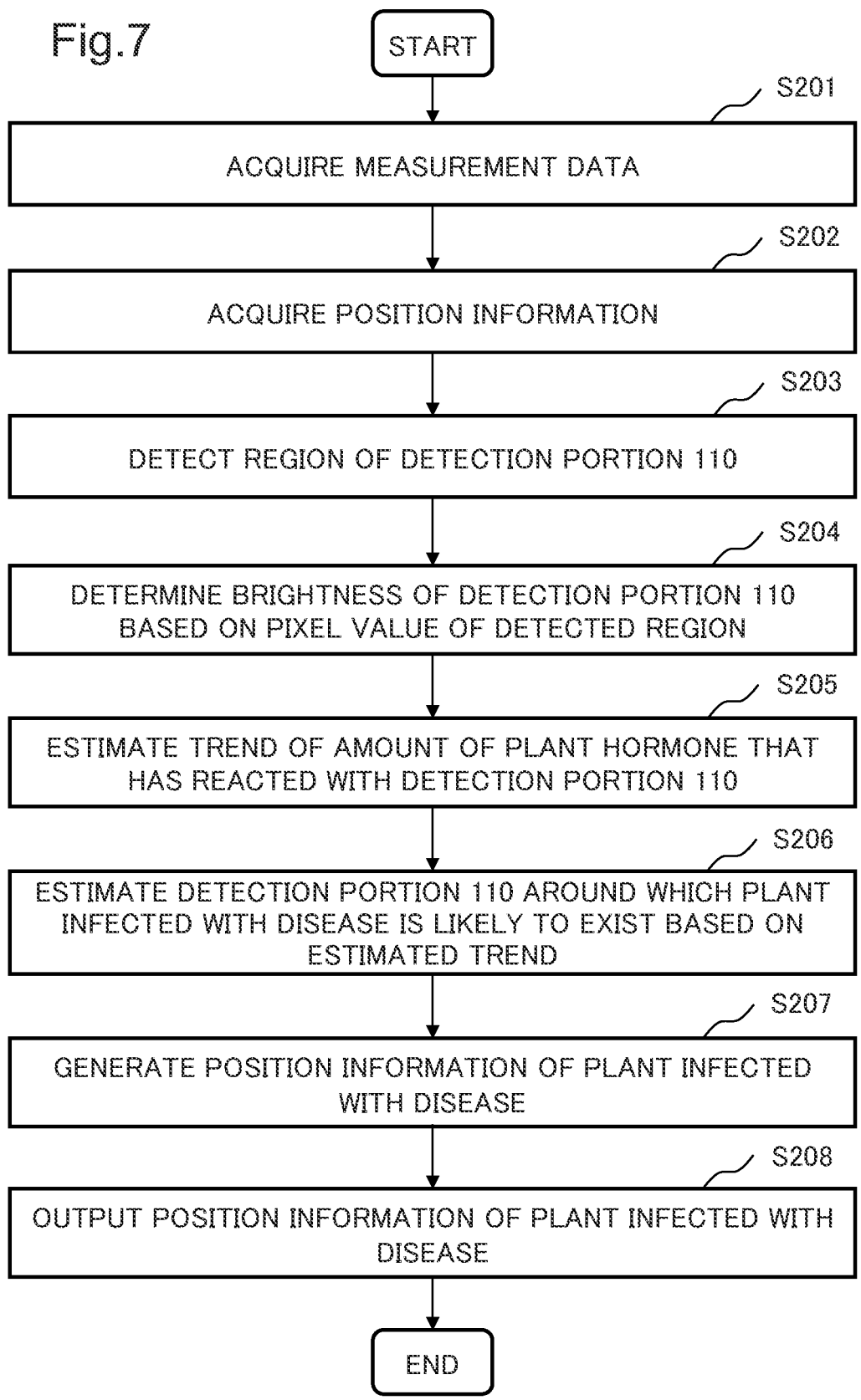
FIG. 7 is a block diagram illustrating an example of an operation of the assistance device according to the fifth example embodiment of the present disclosure.

FIG. 7 is a block diagram illustrating an example of an operation of the assistance device 201 according to the fifth example embodiment of the present disclosure. In the example illustrated in FIG. 7, the measurement data acquisition unit 230 acquires the measurement data (Step S201). The position information acquisition unit 240 acquires the position information (Step S202). Then, the detection unit 250 detects the region of the detection portion 110 from the measurement data (Step S203). The detection unit 250 determines the brightness of the detection portion 110 based on the pixel value of the detected region (Step S204).

The generation unit 210 estimates the trend of the amount of the plant hormone that has reacted with the detection portion 110 based on the trend of the brightness of the region of the detection portion 110 (Step S205). The generation unit 210 estimates the detection portion 110 around which a plant infected with a disease is likely to exist, based on the trend of the amount of the plant hormone that has reacted with the detection portion 110 (Step S206). The generation unit 210 generates the position information of the plant infected with the disease (Step S207). The output unit 220 outputs the position information of the plant infected with the disease (Step S208).

Another Specific Example of Fifth Example Embodiment

The detection device 100 may be attached to a support such as a pillar erected on the ground in a region where a plant is cultivated. A plurality of detection devices 100 may be attached to one pillar at different heights. The detection device 100 may be attached to a support such as a pillar attached to a beam horizontally attached to a ceiling or an upper portion of a greenhouse in which a plant is cultivated. The detection device 100 may be attached to a trunk, a stem, or a branch of a plant. The detection device 100 may be attached to a support attached to a trunk, a stem, or a branch of a plant. The detection device 100 may be a part of a structure onto which the substance is applied. The detection device 100 is a tape impregnated with the substance or a tape on which the substance is applied, and may be wound around a trunk, a stem, or a branch of a plant.

The light source 300 and the sensor 400 may be mounted on a measurement terminal. For example, a person in charge of measurement who holds the measurement terminal may use the measurement terminal to irradiate the detection device 100 with light by using the light source 300, and perform measurement by using the sensor 400 while the detection device 100 is irradiated with light.

The light source 300 and the sensor 400 may be mounted on a mobile object such as a self-propelled robot, a vehicle, or a drone. The mobile object that is a self-propelled robot or a vehicle may irradiate the detection device 100 with light by using the light source 300 and perform measurement by using the sensor 400 during the irradiation of the detection device 100 with light while traveling in a passage in a region where a plant is cultivated. The mobile object that is a flying object such as a drone or a helicopter may irradiate the detection device 100 with light by using the light source 300 and perform measurement by using the sensor 400 during the irradiation of the detection device 100 with light while flying over a region where a plant is cultivated.

The light source 300 may be installed in a place in which a plant is cultivated. While the light source 300 irradiates the detection device 100 with light, the person in charge of measurement may perform measurement by using the sensor 400 that is a digital camera, a camera mounted on a smartphone, or the like, while moving through a passage in a region where a plant is cultivated.

In a case where the sensor 400 is a camera, the position information acquisition unit 240 may receive an image that is the measurement data. The position information acquisition unit 240 may derive the position of the detection device 100 (that is, the position of the detection portion 110) from the image. In this case, a sign indicating the position may be appropriately installed at a place in which the plant is cultivated. In this case, the sensor 400 captures an image in such a way that the region of the detection device 100 and the region of the sign are included in one image. The position information acquisition unit 240 extracts the region of the detection device 100 (or the detection portion 110) and the region of the sign from the image that is the measurement data. Based on the region of the sign, the position information acquisition unit 240 recognizes the position indicated by the sign by using an image recognition technology such as character recognition. The position information acquisition unit 240 specifies the position of the detection device 100 (that is, the detection portion 110) based on a positional relationship between the region of the detection device 100 (or the detection portion 110) and the region of the sign, and the position indicated by the sign. Specifically, the position information acquisition unit 240 may calculate the positions of the detection device 100 (that is, the detection portion 110) and the sign in the place in which the plant is cultivated, from the image including the region of the detection device 100 (that is, the detection portion 110) and the region of the sign. Then, the position information acquisition unit 240 may specify the position of the detection device 100 (that is, the detection portion 110) based on the positional relationship between the detection device 100 (that is, the detection portion 110) and the sign in the place in which the plant is cultivated. The position information acquisition unit 240 may specify the position of the detection device 100 (that is, the detection portion 110) from the image by using another method.

Note that the sensor 400 may have a function of specifying latitude and longitude by using, for example, a global positioning system (GPS) or the like. In this case, the sensor 400 may transmit information on the latitude and longitude specified when the detection portion 110 is measured to the position information acquisition unit 240 as the position information of the detection device 100 including the measured detection portion 110. The position information acquisition unit 240 may use the information on the latitude and longitude received from the sensor 400 as the position information of the detection device 100 including the measured detection portion 110.

The sensor 400 may be one camera or a plurality of cameras fixed to a place in which a plant is cultivated (for example, in a greenhouse).

Instead of the detection device 100, the detection device 101 according to the second example embodiment may be used.

In this case, the person in charge of measurement operates the shielding portion 130 of the detection device 101 in such a way as not to shield the reference portion 120. Then, the person in charge of measurement measures (in other words, captures an image of) the detection device 101 by using the sensor 400 in such a way that the image includes the region of the detection portion 110 and the region of the reference portion 120 that is not being shielded by the shielding portion 130. The person in charge of measurement may perform the measurement of the detection device 101 by using the sensor 400 after operating the shielding portions 130 of all the detection devices 101 in such a way as not to shield the reference portions 120. Once the measurement of the detection device 101 is completed, the person in charge of measurement operates the shielding portions 130 of all the detection devices 101 in such a way as to shield the reference portions 120.

The detection unit 250 extracts the region of the detection portion 110 and the region of the reference portion 120 from the image that is the measurement data. Then, a value representing the brightness of the region of the detection portion 110 and a value representing the brightness of the region of the reference portion 120 are determined. The value representing the brightness of the region of the reference portion 120 is, for example, a representative value (an average value, a median value, an intermediate value, a mode value, or the like) of the pixel values of the pixels included in the region of the reference portion 120. The detection unit 250 uses the same type of representative values as the value representing the brightness of the region of the detection portion 110 and the value representing the brightness of the region of the reference portion 120. The detection unit 250 stores, instead of the value representing the brightness of the region of the detection portion 110, the value representing the brightness of the region of the detection portion 110 and the value representing the brightness of the region of the reference portion 120 in the measurement data storage unit 260 as a part of the trend of the measurement data.

The generation unit 210 reads the trend of the measurement data from the measurement data storage unit 260, and calculates a difference between the value representing the brightness of the region of the detection portion 110 and the value representing the brightness of the region of the reference portion 120 in the trend of the measurement data. The generation unit 210 estimates the trend of the amount of the plant hormone that has reacted with the detection portion 110 based on the amount of change in difference between the value representing the brightness of the region of the detection portion 110 and the value representing the brightness of the region of the reference portion 120 in the trend of the measurement result.

Specifically, for example, the generation unit 210 holds in advance a relationship between the difference between the value representing the brightness of the region of the detection portion 110 and the value representing the brightness of the region of the reference portion 120 and the amount of the plant hormone that has reacted with the detection portion 110 per unit area. The generation unit 210 estimates the amount of the plant hormone that has reacted with the detection portion 110 per unit area from the calculated difference in brightness based on the held relationship.

Instead of the detection device 100, the detection device 102 according to the third example embodiment may be used.

For example, in a case where the sensor 400 is a camera, and the camera can measure the identification information portion 140, the position information acquisition unit 240 receives an image that is the measurement data, and detects a region of the identification information portion 140 in the received image. Then, the position information acquisition unit 240 extracts the identification information indicated by the identification information portion 140 from the region of the identification information portion 140 of the image. As a method of extracting the identification information indicated by the identification information portion 140, an existing method appropriate for the type of the identification information can be used. The position information acquisition unit 240 specifies the position of the measured detection device 102 (that is, the position of the measured detection portion 110) from the extracted identification information based on a relationship between the identification information and a place in which the detection device 102 including the identification information portion 140 indicating the identification information is installed. The position information acquisition unit 240 holds in advance the relationship between the identification information and the place in which the detection device 102 including the identification information portion 140 indicating the identification information is installed. For example, the position information acquisition unit 240 specifies the place in which the detection device 102 including the identification information portion 140 indicating the extracted identification information is installed, in information indicating the held relationship.

In a case where the identification information portion 140 is an RFID tag, the sensor 400 includes, for example, a camera and an RFID reader. The RFID reader of the sensor 400 reads the identification information from the identification information portion 140 that is an RFID tag. In this case, the sensor 400 transmits the read identification information to the position information acquisition unit 240.

The identification information portion 140 may be a module that specifies the position information (that is, the information on the latitude and longitude) by using GPS. In this case, the sensor 400 acquires the specified position information from the identification information portion 140, and transmits the acquired position information to the position information acquisition unit 240.

The position information acquisition unit 240 receives, from the sensor 400, the identification information read from the identification information portion 140 that is an RFID tag. The position information acquisition unit 240 specifies the position of the measured detection device 102 (that is, the position of the measured detection portion 110) from the received identification information based on a relationship between the identification information and a place in which the detection device 102 including the identification information portion 140 indicating the identification information is installed. Also in this case, the position information acquisition unit 240 holds in advance the relationship between the identification information and the place in which the detection device 102 including the identification information portion 140 indicating the identification information is installed. For example, the position information acquisition unit 240 specifies the place in which the detection device 102 including the identification information portion 140 indicating the received identification information is installed, in information indicating the held relationship.

In a case where the detection device 100 is a thread, a string, a tape, a cable, an optical fiber that leaks light, or the like, the detection device 100 may be stretched between a plurality of pillars. The detection device 100 may be suspended from a support such as a pillar. The position information acquisition unit 240 specifies, for example, the position of a portion of the detection device 100 in the image where the intensity of fluorescence is maximum. The position of the portion where the intensity of fluorescence is maximum may be represented by, for example, a distance from any one end of the detection device 100 in a three-dimensional space. In this case, the position information acquisition unit 240 specifies the position of a portion of the detection device 100 in the image where the intensity of fluorescence is maximum. Then, the position information acquisition unit 240 may calculate the distance from any one end of the detection device 100 in the three-dimensional space based on a camera parameter of the camera that serves as the sensor 400. The position information acquisition unit 240 may further use the shape of the detection device 100 measured in advance to calculate the distance from any one end of the detection device 100 in the three-dimensional space.

The detection unit 250 determines whether the portion of the image detection device 100 in the image where the intensity of fluorescence detected by the position information acquisition unit 240 is maximum is a portion where the intensity of fluorescence detected in the past is maximum in the history of measurement results. Specifically, the detection unit 250 detects, in the history of the measurement results, a portion from which a distance to the portion where the detected intensity of fluorescence is maximum (hereinafter, also referred to as maximum intensity portion) is equal to or less than a predetermined distance and in which the detected intensity of fluorescence is maximum (hereinafter, also referred to as past maximum intensity portion). The detection unit 250 stores a value representing the brightness of the maximum intensity portion in the measurement data storage unit 260 as the latest measurement result of the brightness of the detected past maximum intensity portion in the history of the measurement results. In a case where the past maximum intensity portion has not been detected, the detection unit 250 stores a value representing the brightness of the maximum intensity portion in the measurement data storage unit 260 as a new value of the brightness of the portion where the intensity of fluorescence is maximum in the history of the measurement results.

In a case where the detection device 100 is, for example, an optical fiber onto which the substance is applied and which leaks light, the light source 300 irradiates the applied substance with light via the detection device 100 that is the optical fiber.

In a case where the shape of the detection portion 110 represents the identification information of the detection device 102 including the detection portion 110, the detection portion 110 also operates as the identification information portion 140. In this case, the outline of the detection portion 110 may be drawn by using a substance that emits fluorescence when irradiated with light regardless of the presence or absence of the plant hormone. The shape of the detection portion 110 may be, for example, a predetermined figure, a character, or the like.

In this case, the position information acquisition unit 240 detects the region of the detection portion 110 from the image that is the measurement data. Note that, instead of the position information acquisition unit 240, the detection unit 250 may detect the region of the detection portion 110. The position information acquisition unit 240 recognizes the shape of the detection portion 110 detected. In this case, a shape that most matches the shape of the detection portion 110 among a plurality of predetermined shapes is estimated using any one of existing methods in which transformation such as affine transformation or perspective transformation and template matching are combined. The position information acquisition unit 240 may estimate the shape of the detection portion 110 in the three-dimensional space by using any one of existing methods using the camera parameter and the like. Then, the position information acquisition unit 240 may estimate a shape that most matches the estimated shape of the detection portion 110 among a plurality of predetermined shapes. The position information acquisition unit 240 holds in advance a combination of the shape of a figure and information indicating a place in which the detection device 102 including the detection portion 110 having the shape is installed, for each of a plurality of predetermined shapes. Then, the position information acquisition unit 240 determines that the place in which the detection device 102 is installed and which is combined with the shape that most matches the estimated shape of the detection portion 110 is the place in which the detection device 102 including the measured detection portion 110 is installed.

In a case where the shape of the detection portion 110 is a character, the position information acquisition unit 240 performs character recognition on a region including the region of the detection portion 110 by using any one of existing technologies for recognizing a character in a captured image. In this case, the position information acquisition unit 240 holds in advance a combination of a character and a place in which the detection device 102 including the detection portion 110 having the shape of the character is installed, for a plurality of predetermined characters. The position information acquisition unit 240 determines that the place in which the detection device 102 is installed and which is combined with the character recognized by the above-described character recognition is the place in which the detection device 102 including the detection portion 110 on which the above-described character recognition has been performed is installed.

Effects

The present example embodiment has the same effect as those of the fourth example embodiment. The reason is the same as the reason why the effects of the fourth example embodiment are exhibited.

Modified Example of Fifth Example Embodiment

The sensor 400 may be a photodetector having sensitivity to a wavelength of fluorescence emitted by the detection portion 110 irradiated with light. In this case, the measurement data is a value representing the brightness. Then, the detection unit 250 stores a value representing the brightness indicated by the measurement data acquired by the measurement data acquisition unit 230 in the measurement data storage unit 260.

Sixth Example Embodiment

Figure 8:
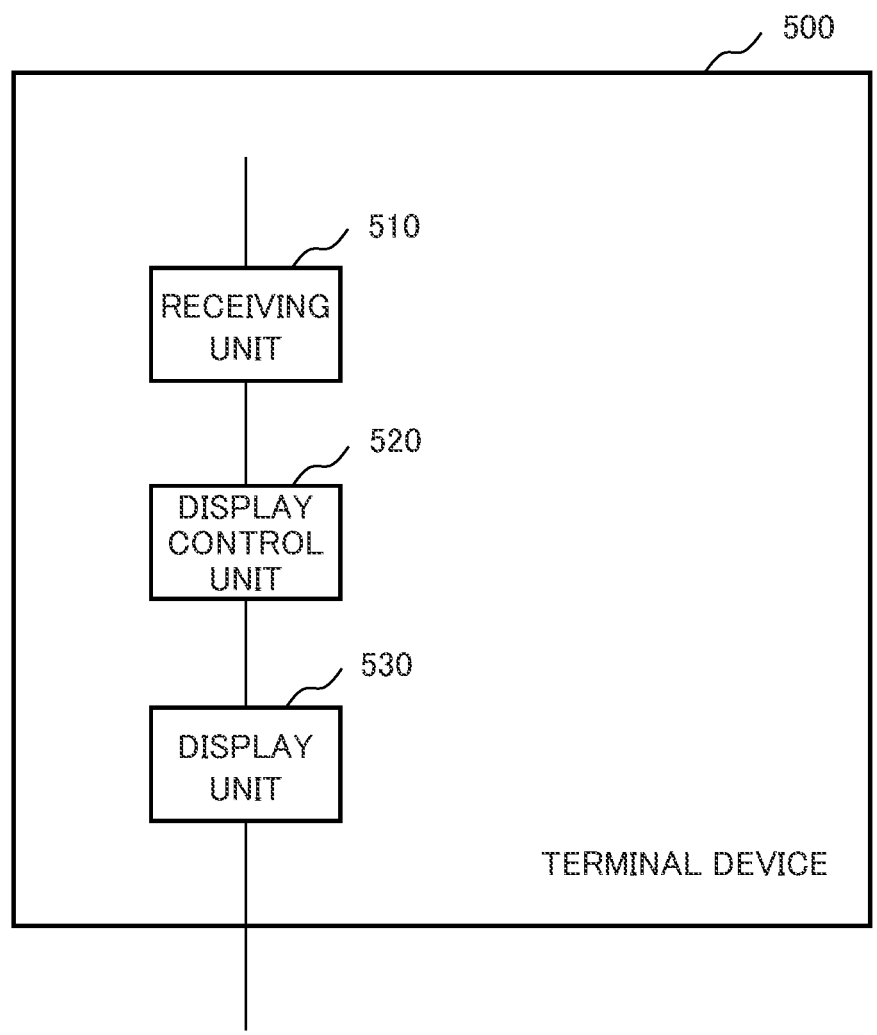
FIG. 8 is a block diagram illustrating an example of a configuration of a terminal device according to a sixth example embodiment of the present disclosure.

FIG. 8 is a block diagram illustrating an example of a configuration of a terminal device 500 according to a sixth example embodiment of the present disclosure. The terminal device 500 of the present example embodiment is the same as the terminal device 500 according to the fifth example embodiment. The terminal device 500 of the present example embodiment is connected to the assistance device 201 according to the fifth example embodiment.

<Terminal Device 500>

The terminal device 500 includes an information receiving unit 510, a display control unit 520, and a display unit 530. The terminal device 500 can be implemented by, for example, a terminal device such as a smartphone, a tablet terminal, or a notebook personal computer.

The information receiving unit 510 receives the position information of the infected plant from the output unit 220 of the assistance device 201. The display control unit 520 controls the display unit 530 to display the received position information of the infected plant. The display unit 530 displays the position information of the infected plant. The display unit 530 is, for example, a display.

Modified Example of Sixth Example Embodiment

The terminal device 500 may be connected to the assistance device 200 according to the fourth example embodiment.

Other Example Embodiments

The assistance device 200 and the assistance device 201 described above can be implemented by a computer including a memory into which a program read from a storage medium is loaded and a processor that executes the program. The assistance device 200 and the assistance device 201 can also be implemented by dedicated hardware. The assistance device 200 and the assistance device 201 can also be implemented by a combination of the above-described computer and dedicated hardware.

Figure 9:
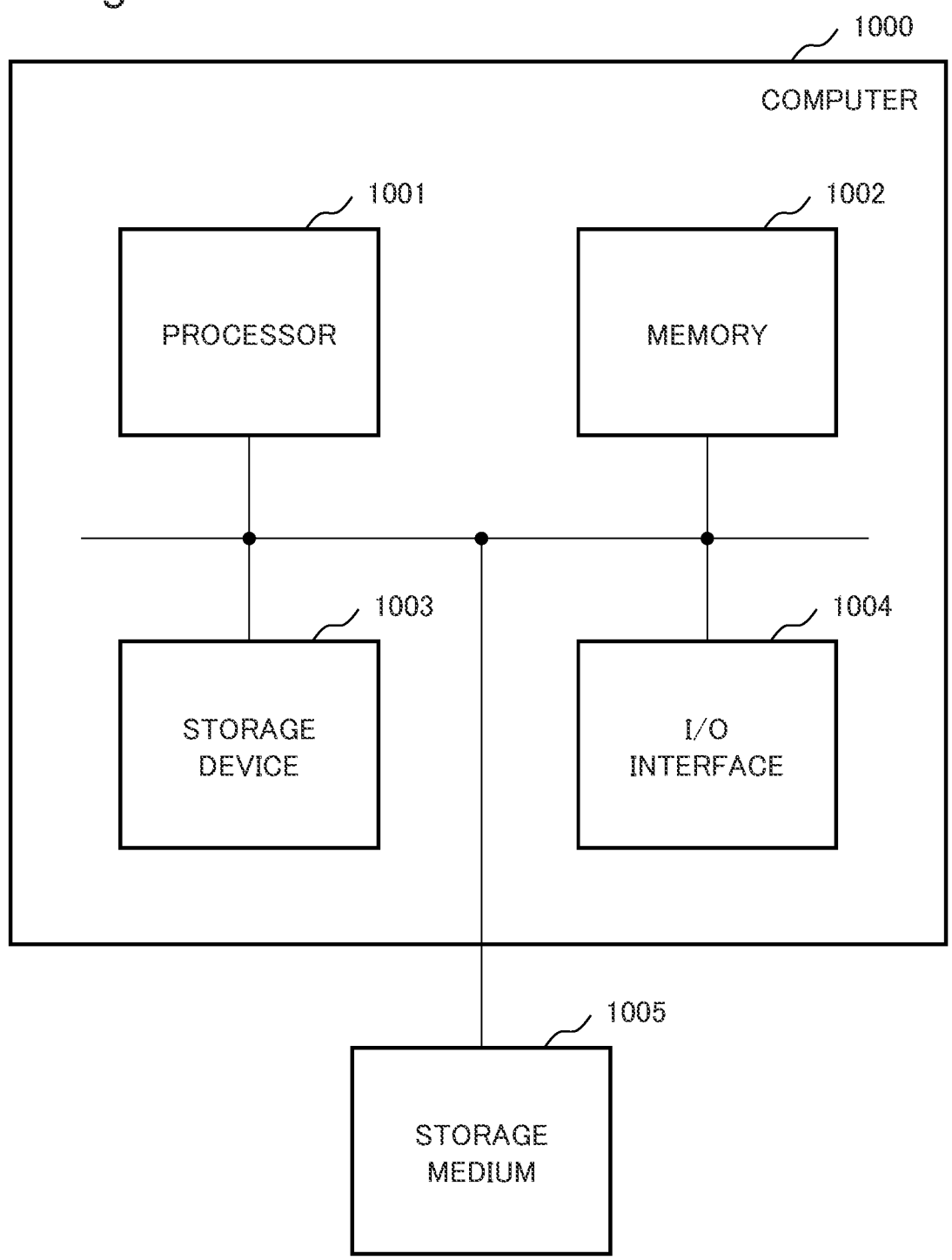
FIG. 9 is a diagram illustrating an example of a hardware configuration of a computer that can implement the assistance devices according to the above-described example embodiments.

FIG. 9 is a diagram illustrating an example of a hardware configuration of a computer 1000 that can implement the assistance devices 200 and 201 according to the above-described example embodiments. Referring to FIG. 9, the computer 1000 includes a processor 1001, a memory 1002, a storage device 1003, and an input/output (I/O) interface 1004. In addition, the computer 1000 can access a storage medium 1005. The memory 1002 and the storage device 1003 are, for example, storage devices such as a random access memory (RAM) and a hard disk. The storage medium 1005 is, for example, a storage device such as a RAM or a hard disk, a read only memory (ROM), or a portable storage medium. The storage device 1003 may be the storage medium 1005. The processor 1001 can read and write data and programs from and in the memory 1002 and the storage device 1003. The processor 1001 can access, for example, the sensor 400 and the terminal device 500 via the I/O interface 1004. The processor 1001 can access the storage medium 1005. The storage medium 1005 stores a program for operating the computer 1000 as the assistance device according to the example embodiment of the present disclosure.

The processor 1001 loads, into the memory 1002, a program that is stored in the storage medium 1005 and causes the computer 1000 to operate as the assistance device according to the example embodiment of the present disclosure. Then, the processor 1001 executes the program loaded into the memory 1002, whereby the computer 1000 operates as the assistance device according to the example embodiment of the present disclosure.

The generation unit 210, the output unit 220, the measurement data acquisition unit 230, the position information acquisition unit 240, and the detection unit 250 can be implemented by, for example, the processor 1001 that executes the program loaded into the memory 1002. The measurement data storage unit 260 can be implemented by the memory 1002 included in the computer 1000 or the storage device 1003 such as a hard disk device. Some or all of the generation unit 210, the output unit 220, the measurement data acquisition unit 230, the position information acquisition unit 240, the detection unit 250, and the measurement data storage unit 260 can be implemented by a dedicated circuit.

Some or all of the above-described example embodiments can also be described as the following Supplementary Notes, but are not limited thereto.

[Supplementary Note 1]
A detection device including:
a detection portion that contains a substance that emits fluorescence in a case of being irradiated with light when reacting with a plant hormone.

[Supplementary Note 2]
The detection device according to Supplementary Note 1, in which the substance emits the fluorescence with an intensity that is in proportion to an amount of the reacted plant hormone.

[Supplementary Note 3]
The detection device according to Supplementary Note 1 or 2, further including:
a reference portion that contains the substance; and
a shielding portion that is detachable and shields the reference portion from outside air.

[Supplementary Note 4]
The detection device according to any one of Supplementary Notes 1 to 3, further including:
an identification information portion that holds identification information in a readable manner.

[Supplementary Note 5]
The detection device according to any one of Supplementary Notes 1 to 4,
in which the substance includes at least one of a boron-oxygen compound having a structure represented by the following General Formula (5) as a receptor that selectively recognizes methyl salicylate, a rare earth compound as a receptor that selectively recognizes methyl salicylate, a zinc compound as a receptor that selectively recognizes methyl salicylate, or a hydrazine derivative as a receptor that selectively recognizes methyl jasmonate.

[Chemical Formula 5]

(5)

[Supplementary Note 6]
An assistance device including:
a generation unit that generates position information of a plant infected with a disease based on a captured image of a detection portion irradiated with light and a position of the detection portion, the detection portion containing a substance that emits fluorescence in a case of being irradiated with the light when reacting with a plant hormone; and an output unit that outputs the generated position information.

[Supplementary Note 7]
The assistance device according to Supplementary Note 6,
in which the substance emits the fluorescence with an intensity that is in proportion to an amount of the reacted plant hormone, and
the generation unit generates the position information based on an amount of change in brightness of the detection portion in the captured image and the position of the detection portion.

[Supplementary Note 8]
The assistance device according to Supplementary Note 6 or 7,
in which the captured image includes a region of the detection portion and a region of a reference portion that is imaged in a state where a shielding portion that is detachable and shields the reference portion containing the substance from outside air is removed from the reference portion, and
the generation unit generates the position information based on the amount of change in difference between the brightness of the detection portion and a brightness of the reference portion in the captured image.

[Supplementary Note 9]
The assistance device according to any one of Supplementary Notes 6 to 8,
in which the generation unit generates, as the position information, a distribution of a degree of possibility that a plant infected with a disease exists in a place in which the detection portion is disposed.

[Supplementary Note 10]
The assistance device according to any one of Supplementary Notes 6 to 8,
in which the substance includes at least one of a boron-oxygen compound having a structure represented by General Formula (1) as a receptor that selectively recognizes methyl salicylate, a rare earth compound as a receptor that selectively recognizes methyl salicylate, a zinc compound as a receptor that selectively recognizes methyl salicylate, or a hydrazine derivative as a receptor that selectively recognizes methyl jasmonate.

[Supplementary Note 11]
An assistance system including:
the assistance device according to any one of Supplementary Notes 6 to 10;
a detection device including the detection portion;
an imaging device that captures the captured image; and
a terminal device that receives the position information and displays the position information.

Supplementary Note 12
A terminal device including:
a receiving unit that receives position information of a plant infected with a disease, the position information being generated based on a captured image of a detection portion irradiated with light and a position of the detection portion, and the detection portion containing a substance that emits fluorescence in a case of being irradiated with the light when reacting with a plant hormone; and
a display unit that displays the received position information.

[Supplementary Note 13]
The terminal device according to Supplementary Note 12, further including:
a receiving unit that receives the position information from an assistance device including a generation unit that generates the position information and an output unit that outputs the generated position information; and
a display control unit that controls the display unit to display the received position information.

[Supplementary Note 14]
The terminal device according to Supplementary Note 13,
in which the substance emits the fluorescence with an intensity that is in proportion to an amount of the reacted plant hormone, and
the generation unit generates the position information based on the amount of change in brightness of the detection portion in the captured image and the position of the detection portion.

[Supplementary Note 15]
The terminal device according to Supplementary Note 13 or 14,
in which the captured image includes a region of the detection portion and a region of a reference portion that is imaged in a state where a shielding portion that is detachable and shields the reference portion containing the substance from outside air is removed from the reference portion, and
the generation unit generates the position information based on the amount of change in difference between the brightness of the detection portion and a brightness of the reference portion in the captured image.

[Supplementary Note 16]
The terminal device according to any one of Supplementary Notes 13 to 15,
in which the generation unit generates, as the position information, a distribution of a degree of possibility that a plant infected with a disease exists in a place in which the detection portion is disposed.

[Supplementary Note 17]
The terminal device according to any one of Supplementary Notes 13 to 16,
in which the substance includes at least one of a boron-oxygen compound having a structure represented by General Formula (1) as a receptor that selectively recognizes methyl salicylate, a rare earth compound as a receptor that selectively recognizes methyl salicylate, a zinc compound as a receptor that selectively recognizes methyl salicylate, or a hydrazine derivative as a receptor that selectively recognizes methyl jasmonate.

[Supplementary Note 18]
An assistance method including:
generating position information of a plant infected with a disease based on a captured image of a detection portion irradiated with light and a position of the detection portion, the detection portion containing a substance that emits fluorescence in a case of being irradiated with the light when reacting with a plant hormone; and
outputting the generated position information.

[Supplementary Note 19]
The assistance method according to Supplementary Note 18,
in which the substance emits the fluorescence with an intensity that is in proportion to an amount of the reacted plant hormone, and
the assistance method further includes generating the position information based on the amount of change in brightness of the detection portion in the captured image and the position of the detection portion.

[Supplementary Note 20]
The assistance method according to Supplementary Note 18 or 19,
in which the captured image includes a region of the detection portion and a region of a reference portion that is imaged in a state where a shielding portion that is detachable and shields the reference portion containing the substance from outside air is removed from the reference portion, and
the assistance method further includes generating the position information based on the amount of change in difference between the brightness of the detection portion and a brightness of the reference portion in the captured image.

[Supplementary Note 21]
The assistance method according to any one of Supplementary Notes 18 to 20, further including:
generating, as the position information, a distribution of a degree of possibility that a plant infected with a disease exists in a place in which the detection portion is disposed.

[Supplementary Note 22]
The assistance method according to any one of Supplementary Notes 18 to 21,
in which the substance includes at least one of a boron-oxygen compound having a structure represented by General Formula (1) as a receptor that selectively recognizes methyl salicylate, a rare earth compound as a receptor that selectively recognizes methyl salicylate, a zinc compound as a receptor that selectively recognizes methyl salicylate, or a hydrazine derivative as a receptor that selectively recognizes methyl jasmonate.

[Supplementary Note 23]
A program for causing a computer to perform:
generation processing of generating position information of a plant infected with a disease based on a captured image of a detection portion irradiated with light and a position of the detection portion, the detection portion containing a substance that emits fluorescence in a case of being irradiated with the light when reacting with a plant hormone; and
output processing of outputting the generated position information.

[Supplementary Note 24]

The program according to Supplementary Note 23,
in which the substance emits the fluorescence with an intensity that is in proportion to an amount of the reacted plant hormone, and
the generation processing includes generating the position information based on the amount of change in brightness of the detection portion in the captured image and the position of the detection portion.

[Supplementary Note 25]

The program according to Supplementary Note 23 or 24,
in which the captured image includes a region of the detection portion and a region of a reference portion that is imaged in a state where a shielding portion that is detachable and shields the reference portion containing the substance from outside air is removed from the reference portion, and
the generation processing includes generating the position information based on the amount of change in difference between the brightness of the detection portion and a brightness of the reference portion in the captured image.

[Supplementary Note 26]

The program according to any one of Supplementary Notes 23 to 25,
in which the generation processing includes generating, as the position information, a distribution of a degree of possibility that a plant infected with a disease exists in a place in which the detection portion is disposed.

[Supplementary Note 27]

The program according to any one of Supplementary Notes 23 to 26,
in which the substance includes at least one of a boron-oxygen compound having a structure represented by General Formula (1) as a receptor that selectively recognizes methyl salicylate, a rare earth compound as a receptor that selectively recognizes methyl salicylate, a zinc compound as a receptor that selectively recognizes methyl salicylate, or a hydrazine derivative as a receptor that selectively recognizes methyl jasmonate.

In the technology described in International Publication No. WO 2021/111621, it is not possible to recognize the presence of a plant with an early-stage disease before the plant is spotted.

The present disclosure has an effect of enabling recognition of the presence of a plant with an early-stage disease.

While the present disclosure has been particularly shown and described with reference to exemplary embodiments thereof, the present disclosure is not limited to these embodiments. It will be understood by those of ordinary skill in the art that various changes in form and details may be made therein without departing from the spirit and scope of the present disclosure as defined by the claims.

What is claimed is:

1. A detection device comprising:
a detection portion that contains a substance that emits fluorescence in a case of being irradiated with light when reacting with a plant hormone.

2. The detection device according to claim 1, wherein
the substance emits the fluorescence with an intensity that is in proportion to an amount of the reacted plant hormone.

3. The detection device according to claim 1, further comprising:
a reference portion that contains the substance; and
a shielding portion that is detachable and shields the reference portion from outside air.

4. The detection device according to claim 1, further comprising:
an identification information portion that holds identification information in a readable manner.

5. The detection device according to claim 1, wherein
the substance includes at least one of a boron-oxygen compound having a structure represented by General Formula (1) as a receptor that selectively recognizes methyl salicylate, a rare earth compound as a receptor that selectively recognizes methyl salicylate, a zinc compound as a receptor that selectively recognizes methyl salicylate, or a hydrazine derivative as a receptor that selectively recognizes methyl jasmonate

[Chemical Formula 1]

(1)

6. An assistance device comprising:
at least one memory configured to store instructions; and
at least one processor configured to execute the instructions to:
generate position information of a plant infected with a disease based on a captured image of a detection portion irradiated with light and a position of the detection portion, the detection portion containing a substance that emits fluorescence in a case of being irradiated with the light when reacting with a plant hormone; and
output the generated position information.

7. The assistance device according to claim 6, wherein
the captured image includes a region of the detection portion and a region of a reference portion that is imaged in a state where a shielding portion that is detachable and shields the reference portion containing the substance from outside air is removed from the reference portion, and
the at least one processor is further configured to generate the position information based on an amount of change in difference between a brightness of the detection portion and a brightness of the reference portion in the captured image.

8. The assistance device according to claim 6, wherein
the at least one processor is further configured to generate, as the position information, a distribution of a degree of possibility that a plant infected with a disease exists in a place in which the detection portion is disposed.

9. The assistance device according to claim 6, wherein
the substance includes at least one of a boron-oxygen compound having a structure represented by General Formula (1) as a receptor that selectively recognizes methyl salicylate, a rare earth compound as a receptor that selectively recognizes methyl salicylate, a zinc compound as a receptor that selectively recognizes methyl salicylate, or a hydrazine derivative as a receptor that selectively recognizes methyl jasmonate.

10. An assistance system including the assistance device according to claim 6, comprising:
a detection device including the detection portion;
an imaging device that captures the captured image; and
a terminal device that receives the position information and displays the position information.

11. An assistance method comprising:
  generating position information of a plant infected with a disease based on a captured image of a detection portion irradiated with light and a position of the detection portion, the detection portion containing a substance that emits fluorescence in a case of being irradiated with the light when reacting with a plant hormone; and
  outputting the generated position information.

12. The assistance method according to claim 11, wherein the captured image includes a region of the detection portion and a region of a reference portion that is imaged in a state where a shielding portion that is detachable and shields the reference portion containing the substance from outside air is removed from the reference portion, and
  the assistance method further comprises generating the position information based on an amount of change in difference between a brightness of the detection portion and a brightness of the reference portion in the captured image.

13. The assistance method according to claim 11, further comprising
  generating, as the position information, a distribution of a degree of possibility that a plant infected with a disease exists in a place in which the detection portion is disposed.

14. The assistance method according to claim 11, wherein the substance includes at least one of a boron-oxygen compound having a structure represented by General Formula (1) as a receptor that selectively recognizes methyl salicylate, a rare earth compound as a receptor that selectively recognizes methyl salicylate, a zinc compound as a receptor that selectively recognizes methyl salicylate, or a hydrazine derivative as a receptor that selectively recognizes methyl jasmonate.

15. The assistance method according to claim 11, further comprising:
  capturing, using an imaging device, the captured image of the detection portion included in a detection device;
  receiving, using a terminal device, the position information; and
  displaying, using the terminal device, the position information.

* * * * *